(12) United States Patent
Nguyen-DeMary et al.

(10) Patent No.: US 9,707,120 B2
(45) Date of Patent: Jul. 18, 2017

(54) OSTOMY APPLIANCE

(75) Inventors: Tinh Nguyen-DeMary, Milltown, NJ (US); Mingliang Lawrence Tsai, Holmdel, NJ (US)

(73) Assignee: Convatec Technologies Inc., Las Vegas, NV (US)

( * ) Notice: Subject to any disclaimer, the term of this patent is extended or adjusted under 35 U.S.C. 154(b) by 784 days.

(21) Appl. No.: 12/599,791

(22) PCT Filed: May 9, 2008

(86) PCT No.: PCT/US2008/063244
§ 371 (c)(1),
(2), (4) Date: Nov. 11, 2009

(87) PCT Pub. No.: WO2008/141180
PCT Pub. Date: Nov. 20, 2008

(65) Prior Publication Data
US 2010/0241092 A1 Sep. 23, 2010

Related U.S. Application Data

(60) Provisional application No. 60/917,334, filed on May 11, 2007.

(51) Int. Cl.
| A61F 5/443 | (2006.01) |
| A61F 5/44 | (2006.01) |
| A61F 5/441 | (2006.01) |
| A61F 5/448 | (2006.01) |
| A61F 5/445 | (2006.01) |

(52) U.S. Cl.
CPC ............ *A61F 5/4407* (2013.01); *A61F 5/441* (2013.01); *A61F 5/445* (2013.01); *A61F 2005/4486* (2013.01)

(58) Field of Classification Search
USPC ....... 604/336, 327, 328, 332, 333, 337, 338, 604/339, 343, 344, 335
See application file for complete search history.

(56) References Cited

U.S. PATENT DOCUMENTS

| 2,684,675 A | 7/1954 | Perry |
| 3,884,242 A | 5/1975 | Bazell |
| 3,938,521 A * | 2/1976 | Ritota et al. .................. 604/328 |
| 4,050,461 A | 9/1977 | Ruby |

(Continued)

FOREIGN PATENT DOCUMENTS

WO WO2008141180 A1 11/2008

*Primary Examiner* — Tatyana Zalukaeva
*Assistant Examiner* — Guy K Townsend
(74) *Attorney, Agent, or Firm* — Wilson Sonsini Goodrich & Rosati (57) ABSTRACT

An ostomy appliance comprises a pouch having first and second walls, with an inlet aperture in the first wall. A stoma seal is carried by the second wall, and is disposed generally in register with the inlet aperture for sealing against a stoma in use. An outer coupling element is coupled to the first wall and surrounds the inlet aperture. An inner coupling element for supporting the stoma seal, is coupled to the second wall and/or to the stoma seal. The outer coupling element surrounds a periphery of the inner coupling element. The stoma seal may be of an inflatable type or an insertable type. Manipulation tabs may be provided associated with the inner and outer coupling elements.

39 Claims, 7 Drawing Sheets

(56) References Cited

U.S. PATENT DOCUMENTS

| | | | |
|---|---|---|---|
| 4,137,918 A * | 2/1979 | Bogert | 604/328 |
| 4,209,009 A | 6/1980 | Hennig | |
| 4,210,131 A * | 7/1980 | Perlin | 600/32 |
| 4,406,657 A | 9/1983 | Curutcharry | |
| 4,411,659 A | 10/1983 | Jensen | |
| 4,701,169 A | 10/1987 | Steer | |
| 4,710,182 A * | 12/1987 | Bryson | 604/339 |
| 4,941,869 A | 7/1990 | D'Amico | |
| 4,950,223 A * | 8/1990 | Silvanov | A61F 5/441 128/DIG. 25 |
| 5,269,774 A * | 12/1993 | Gray | 604/343 |
| 5,935,115 A | 8/1999 | Espina | |
| 6,050,982 A * | 4/2000 | Wheeler | 604/332 |
| 6,050,983 A | 4/2000 | Moore | |
| 6,569,081 B1 | 5/2003 | Nielsen | |
| 6,689,111 B2 * | 2/2004 | Mulhauser | A61F 5/445 604/332 |
| 7,258,661 B2 * | 8/2007 | Davies et al. | 600/32 |
| 8,096,980 B2 * | 1/2012 | Cline | 604/332 |
| 8,388,586 B2 * | 3/2013 | Weig | A61F 2/0027 604/101.05 |
| 8,460,259 B2 * | 6/2013 | Tsai | A61F 5/448 604/317 |
| 8,684,982 B2 * | 4/2014 | Nguyen-DeMary | A61F 5/445 604/317 |
| 2005/0075616 A1 * | 4/2005 | Holter | A61F 5/445 604/332 |
| 2005/0177119 A1 * | 8/2005 | Tsai | A61F 5/445 604/332 |
| 2006/0058577 A1 | 3/2006 | Davies | |
| 2006/0069380 A1 * | 3/2006 | Chen | A61F 13/627 604/391 |
| 2006/0206069 A1 * | 9/2006 | Cline | 604/337 |
| 2007/0021651 A1 * | 1/2007 | Gobel | A61F 2/0013 600/31 |
| 2008/0269698 A1 * | 10/2008 | Alexander | A61F 5/445 604/332 |
| 2010/0022976 A1 * | 1/2010 | Weig | A61F 2/0027 604/355 |
| 2010/0069859 A1 * | 3/2010 | Weig | A61F 2/0027 604/335 |
| 2010/0241092 A1 * | 9/2010 | Nguyen-DeMary | A61F 5/4407 604/336 |
| 2012/0078208 A1 * | 3/2012 | Laudick | A61F 5/4405 604/332 |
| 2012/0283678 A1 * | 11/2012 | Nguyen-DeMary | A61F 5/445 604/332 |
| 2014/0148770 A1 * | 5/2014 | Masters | A61F 5/4407 604/344 |

* cited by examiner

OSTOMY APPLIANCE

FIELD OF THE INVENTION

The present invention relates to the field of ostomy appliances. Certain aspects of the invention are particularly, but not exclusively, suitable for ostomy appliances of a type that can be used to control stoma discharge (so called controlled evacuation appliances).

BACKGROUND TO THE INVENTION

The creation of an ostomy (stoma) is the therapy for many suffers of diseases or injury of the gastrointestinal or urinary tract. An ostomy is the rerouting of the tract through the abdominal wall to outside the patient's body. Once a stoma has been created, the patient may need to use a device worn on the body for capturing or containing stomal body waste. This has traditionally been done with an open bag or pouch attached to the body with adhesive patches or constricting belts. Such a pouch collects body waste exuding uncontrolled through the stoma. However, the wearing of such a pouch, which may be necessarily relatively large to accommodate the uncontrolled discharge of body waste, may be an embarrassing experience for many ostomates. The use of such a pouch may require significant changes to a person's public and personal activities.

A controlled evacuation appliance offers the potential for an ostomate to return to some form of normality. The appliance is typically used to block the stoma mouth, in order to retain the body waste temporarily inside the tract. The appliance is deactivatable and/or removable manually when the ostomate desires to discharge the body waste from the stoma. However, there are many practical and challenging difficulties associated with implementing a cost efficient, yet effective and comfortable appliance.

For example, U.S. Pat. No. 4,941,869 describes an ostomy pouch including a plug for blocking the stoma to provide controlled evacuation. However, in order to discharge body waste, the ostomate has to open the pouch, reach his or hand into the pouch interior, and directly remove the plug. Such a pouch has hygiene concerns, because it requires the user (i) to reach into the pouch interior, and (ii) to touch the plug itself, neither of which is likely to be hygienically clean. Opening the pouch may also release odors from the interior. Finally, such a pouch is not well suited for less-dextrous ostomates.

Accordingly, it is desirable to have a controlled evacuation ostomy appliance that is effective, comfortable, cost efficient, easy to use and hygienic.

SUMMARY OF THE INVENTION

The invention provides a controlled evacuation ostomy appliance comprising a pouch, with first and second walls; a first aperture (stomal aperture) in the first (rear) wall for fitting around a stoma; and a stoma seal positioned generally in register with the first aperture.

In one embodiment, the stoma seal is carried by, or otherwise coupled to, the second wall. Coupling the stoma seal to the second wall enables the stoma seal to be manipulated through manipulation of the second wall without having to touch the stoma seal itself. For example, by pulling the second wall away from the first wall, the stoma seal can be withdrawn away from the stoma, in order to permit a discharge.

The pouch further comprises a stoma seal support which is configured for one or both of the following:

(i) At least initially, to present the stoma seal at a predetermined position with respect to the first aperture, such that, when said pouch is fitted to a stoma, the stoma seal is suitably positioned and supported ready to cooperate with the stoma. Such presentation of the stoma seal means that the ostomate does not have to insert his or hand into the pouch interior in order to fit the stoma seal with respect to the stoma. Instead, the stoma seal is already presented and supported at the first aperture.

(ii) To support the stoma seal while the pouch is worn, for example, to prevent the stoma seal from being displaced outwardly from its sealing position. Such support of the stoma seal means that the stoma seal does not have to be self-supporting by the contact with the stoma tissue.

In another embodiment, the stoma seal support comprises a coupling element for forming a releasable coupling with a complementary coupling part. The type of coupling may be one or more of adhesive, mechanical engagement, or frangible.

In an additional embodiment, a first (outer) coupling element is attached to the first wall around the first aperture for enabling the pouch to be releasably attached either to the body or to a body attachment part worn on the body. The stoma seal support comprises a second (inner) coupling element positioned at the first aperture, the second coupling element being surrounded by the outer coupling element. The inner and outer coupling elements can be releasably secured to a complementary coupling part; and/or the inner and outer coupling elements can be releasably attached or attachable to each other.

In a further embodiment, the inner and outer coupling elements are integral with each other, and are connected by frangible connections.

In another embodiment, a first manipulation tab is associated with the outer coupling element and/or the first wall. A second manipulation tab is associated with the inner coupling element and/or the second wall. The manipulation tabs permit a separation force to be applied to one coupling element relative to the other. Additionally, the manipulation tabs permit the first and second walls to be pulled apart to distend the pouch, and avoid pancaking.

In a further embodiment, the stoma seal is inflatable. Inflation enables control over the sealing pressure, and can adapt to different sizes and shapes of stoma. However, a non-inflatable stoma seal may be used.

In a further embodiment, the stoma seal is insertable into the stoma to seal against internal tissue. An insertable seal enables a low external profile, since the seal does not need to occupy significant space outside the stoma. However, a seal that seals external stoma tissue may be used.

Additional features and/or aspects of the invention are defined in the claims and/or apparent from the following description. Although certain features have been highlighted above and in the appended claims, claim protection may be sought for any inventive feature and/or idea described herein and/or illustrated in the drawings, whether or not emphasis has been placed thereon.

DETAILED DESCRIPTION OF PREFERRED EMBODIMENTS

In the accompanying drawings, the same reference numerals are used to depict the same or equivalent features.

Referring to FIGS. 1-5, a first embodiment illustrates a controlled evacuation ostomy appliance in the form of a pouch 10 as a body waste collector. The pouch 10 generally comprises an envelope defined by two walls, a first, rear wall 12 and a second, front wall 14. The walls 12, 14 may be formed from separate sheets secured together around their mutual periphery, or from a single sheet of material that is folded and secured around its edges to define an envelope shape. Each wall 12, 14 may be made of any suitable flexible sheet or film material, such as a laminate including at least one layer of ethylene vinyl acetate (EVA) and at least one gas barrier layer, such as poly(vinylidene chloride) PVDC.

The rear wall 12 comprises, in its upper region, a stomal aperture 16 for fitting around a stoma 18 (FIG. 4) in use. A first (outer) coupling element 20 is attached to the rear wall 12 around the stomal aperture 16. In the present embodiment, the outer coupling element 20 is an adhesive coupling element, including a closed-loop shaped substrate (e.g., a foam tape) carrying adhesive. The outer coupling element 20 includes a first manipulation tab 21 for facilitating manipulation of the pouch 10. The first manipulation tab 21 is associated with the outer coupling element 20 and/or with the rear wall 12. The first manipulation tab 21 may be integral with the substrate of the outer coupling element 20. The first embodiment is a one-piece appliance, in which the pouch 10 is directly coupled to the peristomal skin. The adhesive of the first coupling element 20 is of a skin-compatible type.

The pouch 10 further comprises a stoma seal 22 that is carried by and/or coupled to, the front wall 14. The stoma seal 22 is positioned generally in register with the stomal aperture 16. In the present embodiment, the stoma seal 22 is mounted on the external (or front) side of the front wall 14, and projects through a second aperture 23 in the front wall 14 into the pouch 10 interior. However, the stoma seal 22 could be mounted on the interior face of the front wall 14. Also, in the present embodiment, the stoma seal 22 projects through the stomal aperture 16 so that the distal end of the stoma seal 22 projects through the rear of the pouch 10.

The stoma seal 22 may take any suitable form for sealing against the inner and/or outer surface of the stoma 18. In the present embodiment, the stoma seal 22 is configured to be (i) of an inflatable type, and (ii) of a type that is inserted into the stoma 18 to seal against the internal tissue behind the stoma 18. The stoma seal 22 generally comprises at least one membrane 25 that defines an inflatable balloon 24 arranged around a tube 26. The membrane 25 may be thermoformed into a generally tubular and/or bulbous shape. Such a shape may also be formed by gusseting the membrane material. The tube 26 is made of a generally soft, flexible material, such as silicone rubber. The tube 26 has one or both of the following functions: (i) an inserter guide for facilitating insertion of the inflatable balloon 24 into the stoma 18 when the inflatable balloon 24 is in a deflated condition; and (ii) for delivering inflation fluid to the inflatable balloon 24 from an inflation port 28. The tube 26 is open at its distal end, and may also have openings (not shown) along its length. The tube 26 is fitted, at its proximal end, with an inflation valve 30 defining the inflation port 28. The inflation valve 30 is configured to admit inflation fluid (such as air or saline) when injected by a user, and for preventing escape of the inflation fluid, at least until desired by the ostomate.

The pouch 10 further comprises a stoma seal support for supporting the stoma seal 22. The stoma seal support comprises one or more of the following elements: a second (inner) coupling element 34, a relatively rigid housing 36, and foam 38. The inner coupling element 34 is disposed at the stomal aperture 16 inwardly of the outer coupling element 20. A periphery of the inner coupling element 34 is surrounded by the outer coupling element 20.

It may be convenient to form the outer and inner coupling elements 20, 34 integrally together from a common substrate piece. For example, the two coupling elements 20, 34 may be stamped from a single piece of material. In this case, the outer and inner coupling elements 20, 34 may be coupled together by frangible connections 39 so that, at least initially, the outer and inner coupling elements 20 and 34 are generally coplanar. The adhesive surfaces of the two coupling elements 20 and 34 may be protected by a removable release sheet 40, for example, a plastics sheet coated with a suitable release material such as silicone.

The housing 36 is secured to the outer face of the front wall 14 around the second aperture 23. The proximal end of the tube 26 and/or the inflation port 28 is anchored to the housing 36 at an aperture 42. The housing 36 is made of a material that is more rigid than the pouch walls 12, 14, but may also be resiliently flexible. The housing 36 may have a three-dimensional shape that helps its rigidity, such as a dome shape. The housing 36 (and the foam 38) supports the stoma seal 22 with respect to the front wall 14. The front wall 14 is itself supported in the region of the stomal aperture 16 by means of the inner coupling element 34, thereby supporting the housing 36 and the stoma seal 22. A second manipulation tab 37 carried on a collar 35 is attached to the housing 36 for applying a force to distend the pouch to permit a discharge of body waste, as described later below. The second manipulation tab 37 is associated with the front wall 14 and/or with the inner coupling member 34. The first and second manipulation tabs 21, 37 may be disposed at different angular orientations (FIGS. 2 and 3), to allow easy access using a different hand to hold each tab.

Figure 1:
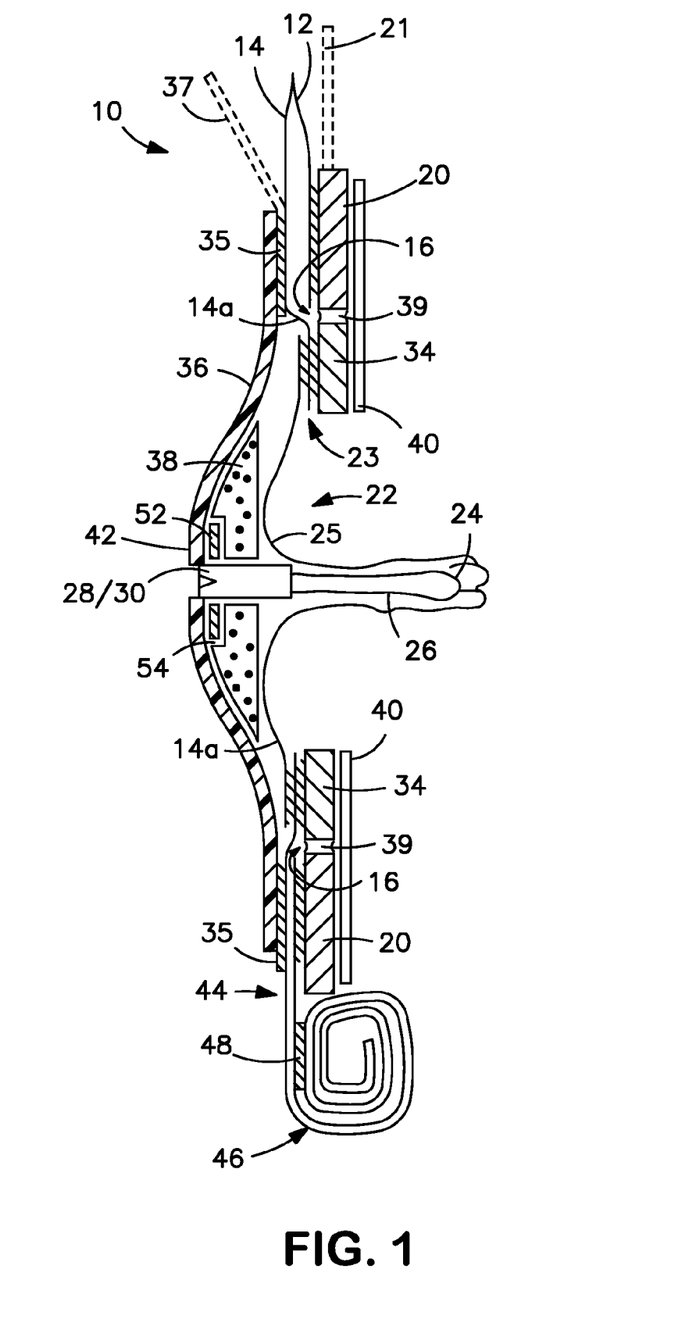
FIG. 1 is a schematic sectional view through a first embodiment of the invention in the form of a one-piece appliance in a deflated condition.
Figure 2:
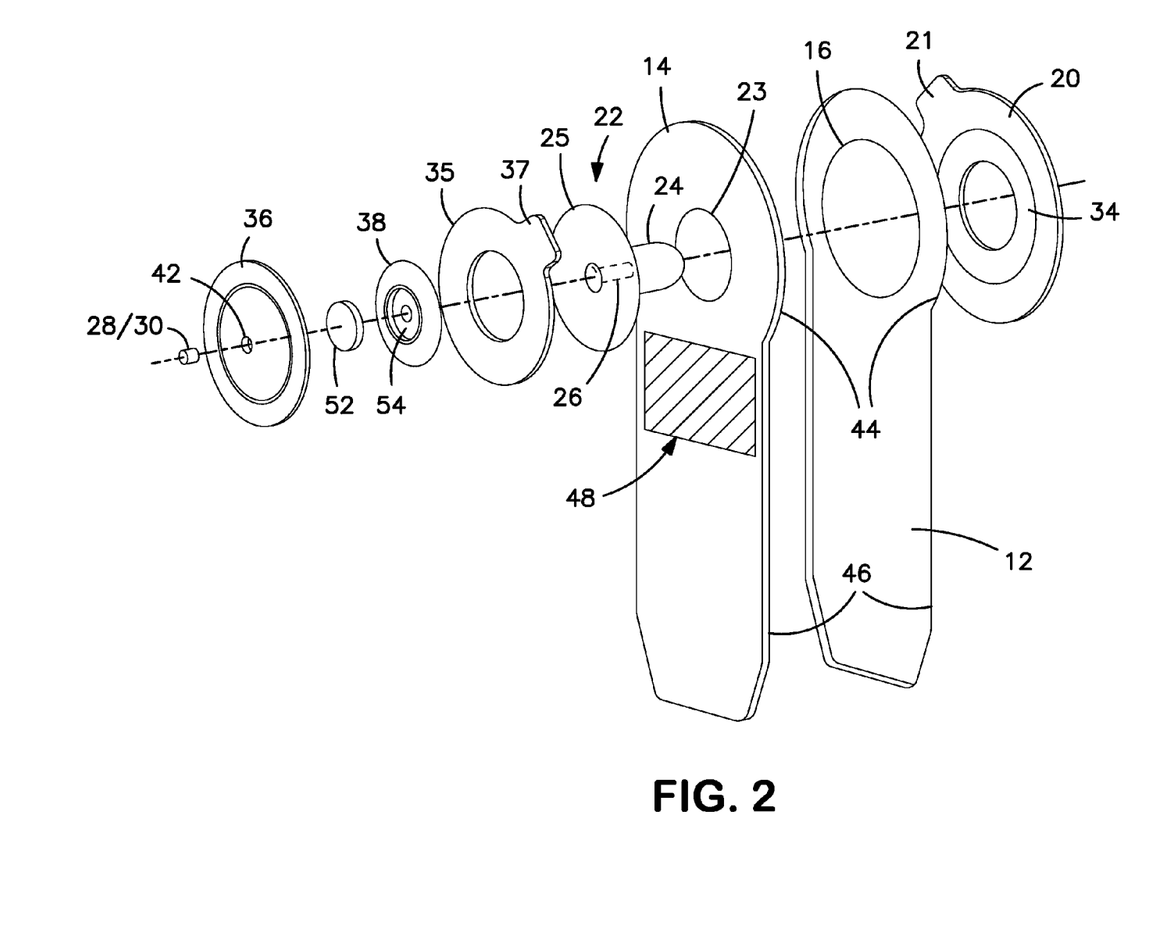
FIG. 2 is an exploded view of the pouch of the first embodiment.
Figure 3:
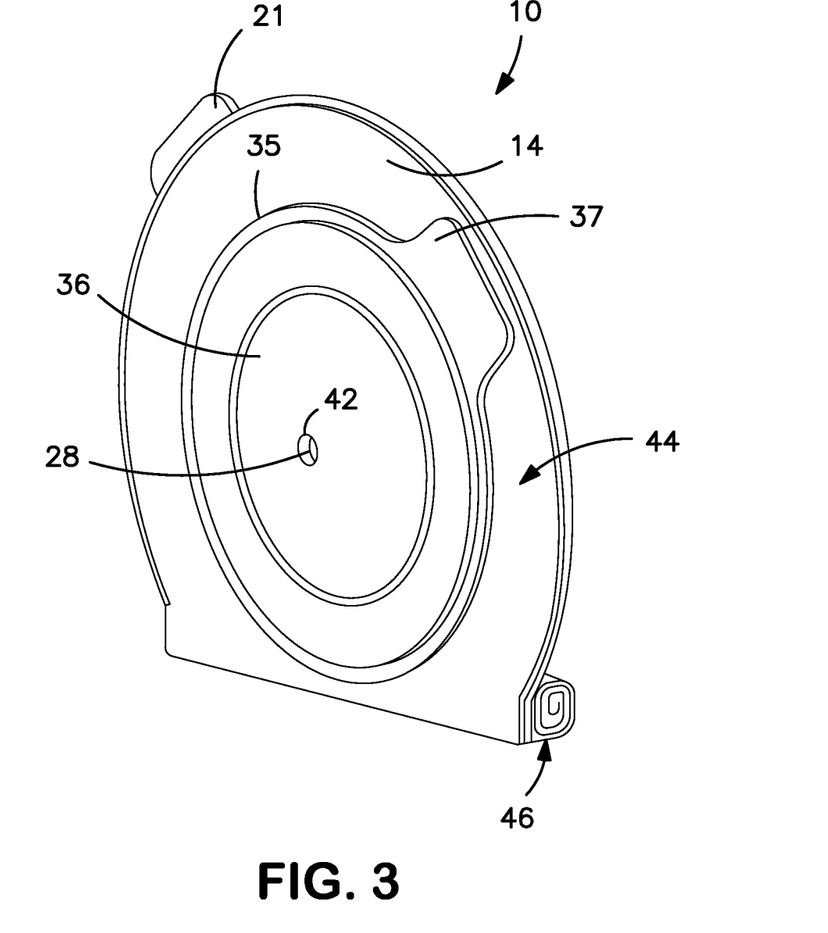
FIG. 3 is a front perspective view of the first embodiment of FIG. 1.
Figure 4:
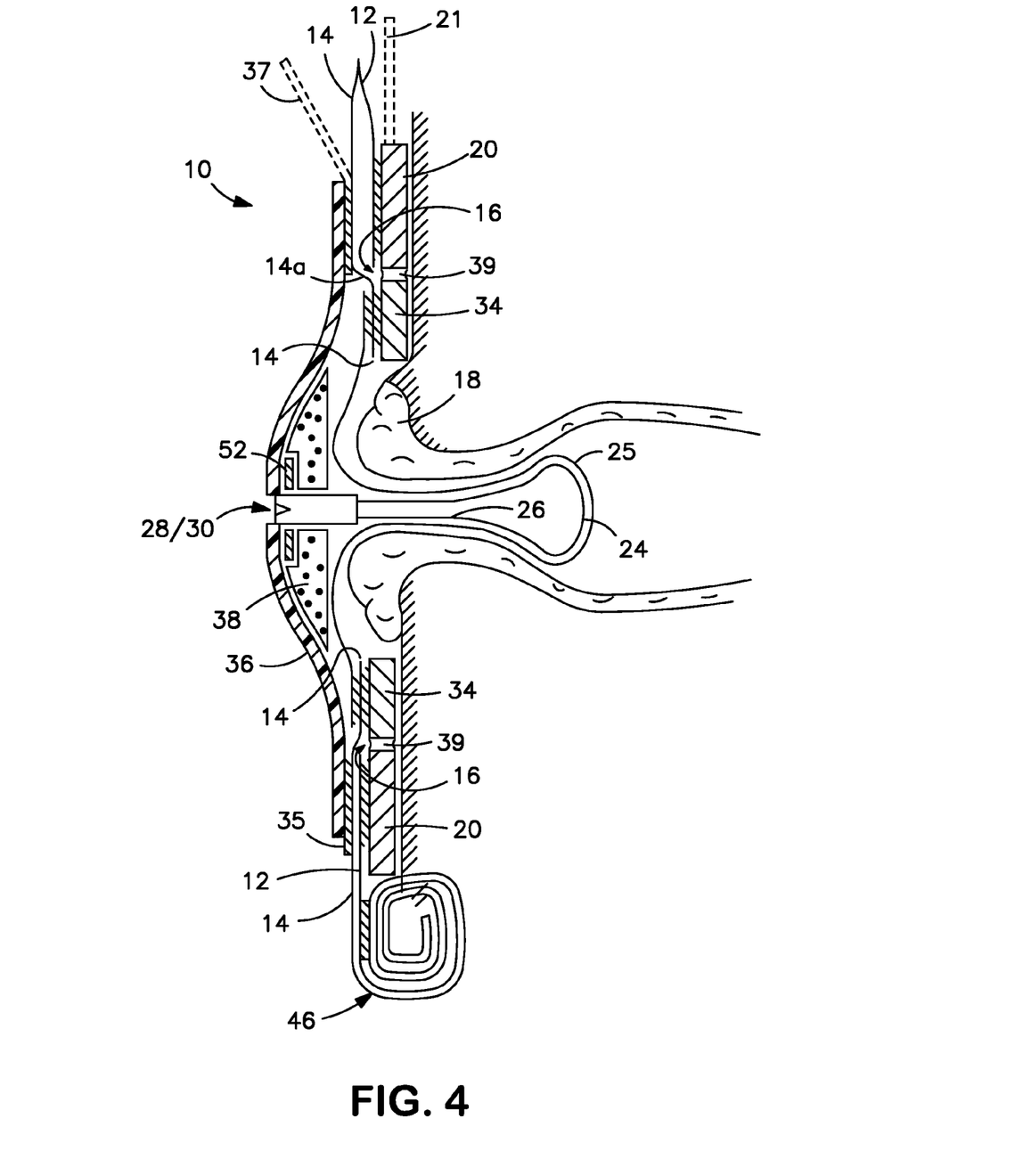
FIG. 4 is a schematic sectional view of the first embodiment in a fitted and deployed condition.

The foam 38 is disposed between the membrane 25 and the housing 36. The foam 38 is of a soft compressible type to provide a cushion between the relatively rigid housing 36 and the membrane 25, and thus prevent discomfort to the stoma 18. As can be seen in FIGS. 1 and 4, an intermediate, annular shaped portion 14a of the front wall 14 optionally exists between the points at which the front wall 14 is fastened to (i) the inner coupling element 34 and (ii) the housing 36. The intermediate portion 14a provides a degree of limited floating movement between the inner coupling element 34 and the housing 36. This floating movement, in combination with the foam 38, provides a degree of decoupling so that the relatively rigid housing 36 does not, in use, cause discomfort to the stoma 18, even if an external force is accidentally applied to the housing 36. Alternatively, in other embodiments, the housing 36 or the stoma seal 22 may be directly attached to the inner coupling element 34 without such floating movement.

The pouch 10 may have any desired shape or profile. In the present embodiment, the pouch 10 generally has a "keyhole" shaped profile. The pouch 10 has an upper rounded or bulbous portion 44 at which the stomal aperture 16 and the coupling elements 20, 34 are located, and from which depends a lower collection portion 46. The lower collection portion 46 may have a (maximum) transverse dimension smaller than the maximum transverse dimension of the upper rounded portion 44. Initially, the lower collection portion 46 is rolled or folded into a compact configuration, to reduce the size of the pouch 10. For example, the lower collection portion 46 may be rolled up to the upper rounded portion 44, and secured in position by means of a pressure sensitive adhesive region 48 on one wall 12 of the pouch 10. Other means such as hook-hook or hook-loop fasteners may be used instead of adhesive if desired, or a flap or sling (not shown) may wrap around or under the rolled-up lower collection portion 46 to hold it in its compact condition. Alternatively, an external clip may be used to hold the lower collection portion 46 in its compact condition.

In the illustrated embodiment, the pouch 10 is a closed pouch, and the lower collection portion 46 is completely closed. Alternatively, the pouch 10 may be of a drainable type, and the lower collection portion 46 may include a drain aperture, such as a drain chute (not shown) or a drain tap (not shown).

Prior to use, the pouch 10 generally has the configuration shown in FIG. 1. The arrangement of the outer and inner coupling elements 20, 34 keeps the pouch 10 generally flat, and presents the deflated balloon 24 of the stoma seal 22 at the stoma aperture 16. The stoma seal 22 is generally presented at position suitable for cooperating with the stoma 18. The outer and inner coupling elements 20, 34 are retained generally co-planar by one or both of: (i) the frangible connections 39; and (ii) the adhesion of both coupling elements 20, 34 to the release sheet 40 (although such adhesion may be relatively weak).

Referring to FIG. 4, once the release sheet 40 is removed, fitting the pouch 10 to a stoma 18 is a straightforward three-stage process. A first stage is to align the pouch 10 with respect to the stoma 18, to insert the distal end of the deflated balloon 24 of the stoma seal 22 into the stoma 18. The tube 26 acts as a guide or introducer for this purpose. The deflated balloon 24 collapses around the tube 26, and the tube 26 enables the balloon 24 to be easily slid into the stoma 18. The softness and flexibility of the tube 26 ensures that the tube 26 does not itself irritate or damage the stoma tissue. The membrane material 25 may be coated with a lubricant and/or the material may be inherently lubricious. The degree of projection of the tube 26 from the stomal aperture 16 can ensure that the user can view the alignment easily, and that the pouch 10 does not obscure the user's view.

Once the balloon 24 has been partially inserted, the next stage is to press the pouch 10 towards the body, so that the balloon 24 fully enters the stoma 18, and the coupling elements 20, 34 contact the wearer's peristomal skin. The co-planarity of the outer and inner coupling elements 20, 34 can ensure that, although the inner coupling element 34 may be entirely surrounded by the outer coupling element 20, the inner coupling element 34 can contact the peristomal skin as equally securely as the outer coupling element 20. The user may press the housing 36 to apply additional pressure to the inner coupling element 34 in order to ensure good adhesive contact. The foam 38 between the housing 36 and the stoma seal 22 avoids pressure applied to the housing 36 from being applied directly to the stoma 18; such pressure could be uncomfortable for the ostomate.

The final stage (FIG. 4) is for the user to inflate the balloon 24 of the stoma seal 22. For example, the user can insert a source of inflation fluid, such as a pump or syringe, into the inflation port 28, in order to inject the inflation fluid to a desired inflation pressure. The inflated balloon 24 presses against the internal tissue of the stoma 18, to effect a seal against discharge of body waste.

An advantage of the above arrangement is that the stoma seal 22 cooperates with the stoma 18 as part of the process of fitting the pouch 10. It is not necessary to reach into the pouch interior to fit the stoma seal 22 in place.

While the pouch 10 is being worn (FIG. 4), the inner coupling element 34, in combination with the housing 36, provides support for the stoma seal 22. In particular, the inner coupling element 34 and the housing 36 resist any tendency for the balloon 24 to be ejected from the stoma 18, for example, by gas or body waste accumulating against the distal end of the balloon 24. With such an arrangement, the balloon 24 does not have to be inflated to a very high pressure, since the balloon 24 is supported externally. The inflation pressure merely has to be moderate to enable an effective seal against leakage of body waste past the balloon 24. The inflation pressure itself does not have to frictionally hold the balloon 24 inside the stoma 18. The balloon 24 may be engineered to permit venting of flatus through or around the balloon 24 to avoid discomfort that may be caused by accumulation of flatus in the intestine.

Flatus venting past or through the stoma seal 22 may be deodorized by means of a deodorizing filter 52. The filter 52 is conveniently located inside the housing 36, and may be accommodated in a recess of pocket 54 of the foam 38. Flatus enters the filter 52 either through the foam 38 and/or through one or more flatus passages (not shown) provided through the membrane 25 and or through the tube 26. Such passages may comprise microporous apertures or perforations in the membrane 25, for example, in a non-inflatable part of the membrane 25. The apertures can be formed by laser. The size of the apertures may be from about 0.005 mm to about 0.5 mm. The outlet side of the filter 52 may communicate with the aperture 42 for discharging the deodorized flatus to the external atmosphere. Alternatively, additional outlet apertures (not shown) may be provided in the housing 36, such apertures having a size of from about 0.1 mm to about 2 mm. The filter 52 may also serve to deodorize odors from body waste collected later in the pouch 10 when the stoma seal 22 is deactivated to permit a discharge.

While the pouch 10 is worn for the first time, the collection portion 46 of the pouch may remain in its compact condition, such that the pouch 10 occupies very little space. The pouch 10 can form a snug fit against the body, and can be worn under most clothing without being obtrusive. The provision of the inner coupling element 34 keeps the front wall 14 of the pouch 10 close to the rear wall 12, and close to skin level. Furthermore, the majority of the structure is made of flexible and low-profile material, giving the appliance a very low profile not substantially more obtrusive than a simple open pouch. The only significant rigid portion of the appliance is the housing 36, but this can be made of material that is resiliently flexible while having a generally self-supporting shape.

Figure 5:
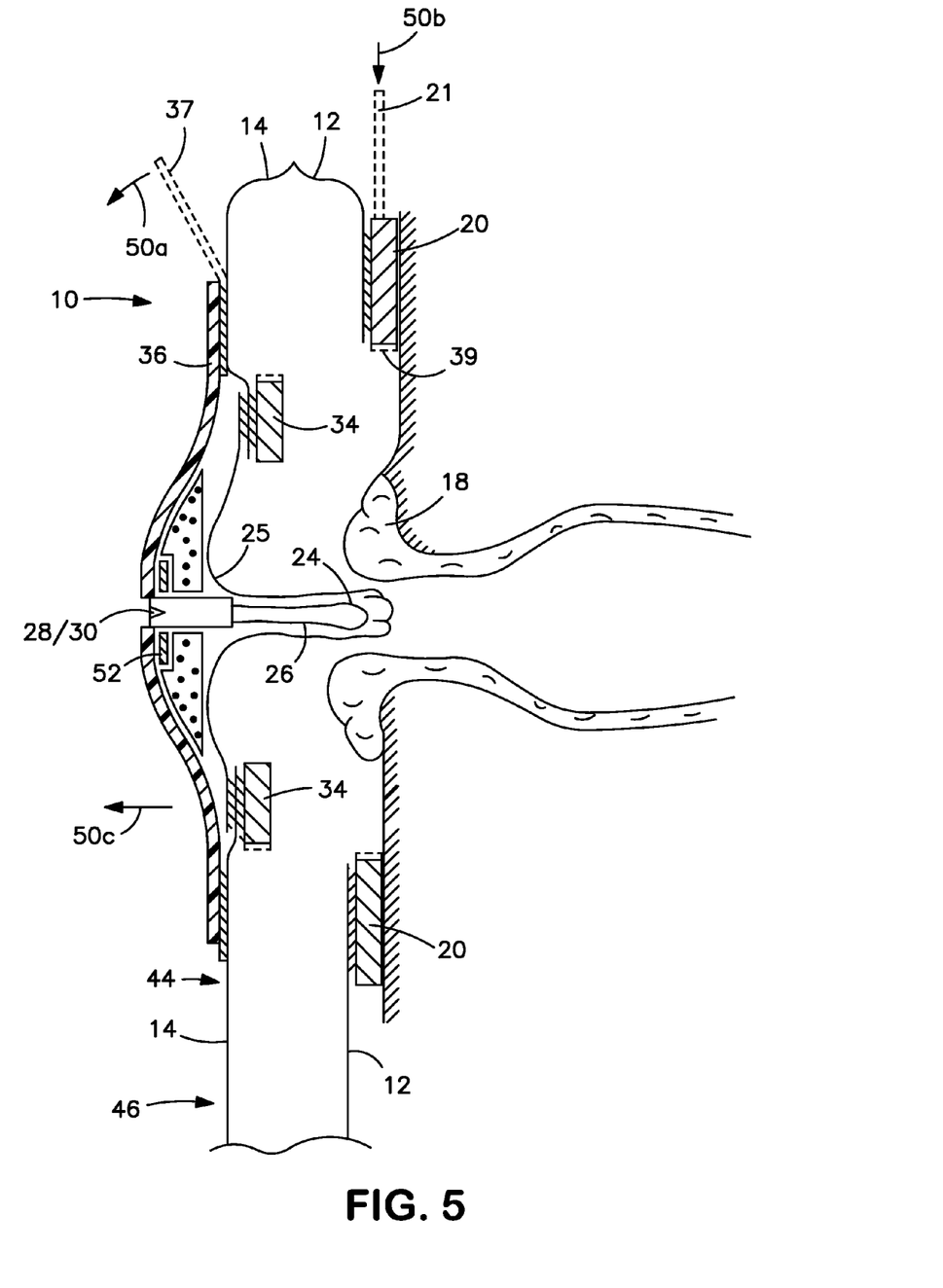
FIG. 5 is a schematic sectional view of the removal of the first embodiment.

Referring to FIG. 5, when the user desires to discharge body waste, the user first manipulates the inflation valve 30 at the inflation port 28 to vent the inflation fluid. This permits the balloon 24 to collapse out of sealing engagement with the stoma tissue. Thereafter, the user distends the upper portion 44 of the pouch 10, in order to withdraw the stoma seal 22 substantially from the stoma 18, and permit discharge of body waste into the pouch 10. To distend the upper portion 44, the user pulls on the second manipulation tab 37 with one hand (arrow 50a), while gripping the first manipulation tab 21 with the other hand (arrow 50b), in order to stabilize the pouch 10. Pulling on the second manipulation tab 37 in a direction away from the stoma 18 causes the inner coupling element 34 to peel out of adhesive contact with the skin. The relative geometry of the housing 36 and the inner coupling element 34 is such that force applied from the second manipulation tab 37 is applied in a direction to peel the inner coupling element 34 progressively. The peeling force is applied from the housing 36 through the intermediate wall portion 14a to the outer edge of the inner coupling element 34. The peeling motion also causes the frangible connections 39 to sever progressively, allowing the inner coupling element 34 to separate from the outer coupling element 20. The user grips the first manipulation tab 21 to directly stabilize the outer coupling element 20 against any peeling, and thus ensure that the outer coupling element 20 remains in firm adhesive contact with the skin.

As the inner coupling element 34 becomes detached from the skin and from the outer coupling element 20, the front wall 14 of the pouch 10 displaces away from the rear wall 12 (arrow 50c), thereby withdrawing the stoma seal 22 from the stoma 18. Depending on the projecting length of the tube 26, the stoma seal 22 may either be completely withdrawn from the stoma 18, or the distal end of the seal 22 may partly remain inside the mouth of the stoma 18, where it does not substantially obstruct stomal discharge of body waste into the pouch 10. The flexibility of the tube 26 and/or the membrane 25 defining the inflatable balloon 24, can ensure that these items can be pushed aside by the exiting body waste. The user may manually extend the lower collection portion 46 of the pouch 10, or the lower collection portion 46 may extend automatically under the weight of body waste entering the pouch 10 and falling into the lower collection portion 46.

A significant advantage of the invention is that the user does not have to insert his or hand into the interior of the pouch 10 in order to deactivate the stoma seal 22. The stoma seal 22 can be deactivated and withdrawn merely by manipulation of the second manipulation tab 37 on the front wall 14.

An additional important effect of providing the second manipulation tab 37 attached to the front wall 14 is that the user manually distends the upper portion 44 of the pouch 10 when effecting a discharge. This can avoid any problem of "pancaking", which sometimes occurs when the internal surfaces of the front and rear walls 12, 14 stick together. By manually distending the upper portion 44 of the pouch 10, the user ensures that stomal discharge can freely enter the pouch.

Depending on the specific design of the pouch 10, the pouch 10 may be intended for a single-sealing use, or for multiple-sealing uses. A single-sealing use may be appropriate if the stoma seal 22 is not intended to be resealed into the stoma 18, for example, if the stoma seal 22 has a limited seal life or is not intended to be re-inflated multiple times. A multiple-sealing use may be appropriate if the stoma seal 22 is of a more substantial type that can be resealed and/or re-inflated reliably.

If the pouch 10 is of a multiple-sealing use type, the user may re-engage the stoma seal 22 without having to (i) remove the pouch 10, nor (ii) insert his or her hand into the pouch interior. Instead, the user can manipulate the stoma seal 22 by means of the second manipulation tab 37, to guide the stoma seal 22 back into the stoma 18. The user may also press against the housing 36 in order to press the inner coupling element 34 into firm adhesive engagement with the skin. The foam 38 can ensure that application of such pressure through the housing 36 does not cause any discomfort to the stoma 18 itself. Thereafter, the user may re-inflate the balloon 24 of the stoma seal 22 in the same manner as described previously.

When it is desired to remove the pouch 10, for example for cleaning or for disposal after a single or final discharge (as appropriate), the user grips the first manipulation tab 21 to peel the outer coupling element 20 out of adhesive engagement with the skin.

Figure 6:
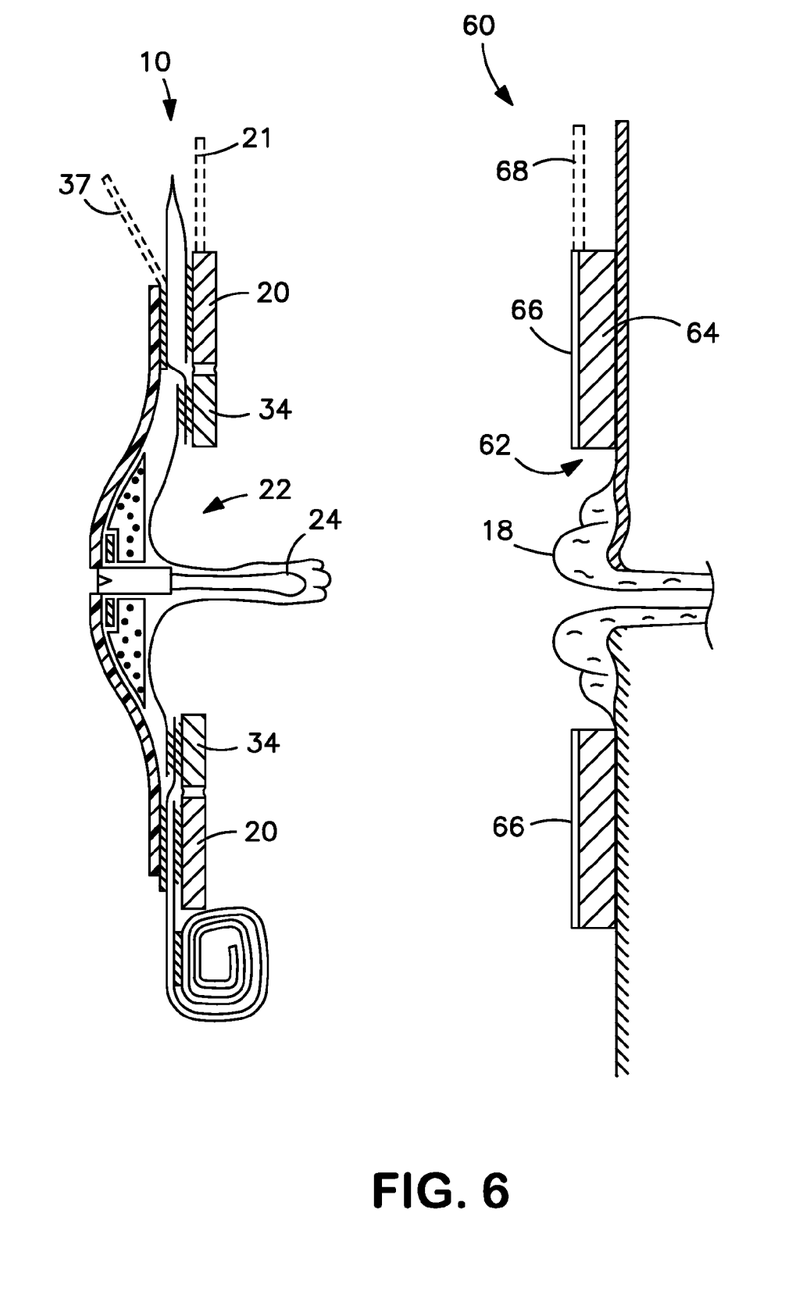
FIG. 6 is a schematic sectional view of a second embodiment of the invention in the form of a two-piece appliance.

FIG. 6 illustrates a second embodiment of the invention in the form of a two-piece appliance. The pouch 10 has the same construction as the first embodiment. The main difference in the second embodiment is that the outer and inner coupling elements 20, 34 do not directly contact the peristomal skin. Instead, a separate body wafer or body fitment 60 is provided for attachment to the skin. The body fitment comprises a third aperture 62, a pad of skin compatible adhesive 64 for attachment to the skin, and a landing surface 66 to which the outer and inner coupling elements 20, 34 of the pouch 10 can adhere. The material of the landing surface 66 and the adhesive 64 of the outer and inner coupling elements 20, 34 are such to enable peelable and re-sealable adhesion. The body fitment 60 further comprises one or more additional manipulation tabs, such as a third manipulation tab 68.

The use of the pouch 10 of the second embodiment is similar to that of the first embodiment, except that the body fitment 60 remains attached to the ostomate when the pouch 10 is removed. The third manipulation tab 68 is used by the ostomate to stabilize the body fitment 60 on the body whenever the outer coupling element 20 or the inner coupling element 34 is to be peeled from the body fitment 60. For example, when distending the upper portion 44 of the pouch 10, the user would grip the second manipulation tab 37 to apply the distension force with one hand, while gripping the third manipulation tab 68 with the other hand to ensure that the body fitment 60 remains firmly attached to the body.

In the second embodiment, the adhesive 64 for the outer and inner coupling elements 20, 34 could be provided on the body fitment 60 instead of on the pouch 10, if desired. The outer and inner coupling elements 20, 34 may then just be substrates for contacting the adhesive surface of the body fitment 60.

In the second embodiment, the outer and inner coupling elements 20, 34 use adhesive 64 to form a releasable coupling. However, in a modification of the second embodiment, the coupling between the body fitment 60 and one or both of the coupling elements 20, 34 may be mechanical instead of adhesive. For example, the outer and inner coupling elements 20, 34 may each comprise a mechanical engagement profile for forming a releasable mechanical engagement with a complementary profile on the body fitment 60.

Also, in the first and second embodiments, an external source of inflation fluid is used to inject inflation fluid for inflating the balloon 24. In a modification of the first and second embodiments, the pouch 10 may include an integral supply of inflation fluid, such as a bulb or concertina pump containing inflation fluid.

Figure 7:
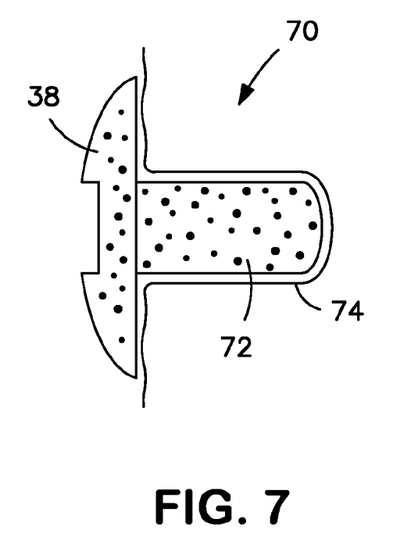
FIG. 7 is a schematic sectional view of a first possible modification of the stoma seal used in the preferred embodiments.

Furthermore, in the first and second embodiments, the stoma seal 22 is inflatable. However, the invention also contemplates a stoma seal 22 that may be non-inflatable. For example, FIG. 7 illustrates a non-inflatable stoma seal 70, comprising a bolster or plug 72 of a soft compressible material, such as a foam 38. The plug 72 may be covered by a flexible film material 74 that contacts the stoma tissue. The plug 72 may be integral with the foam 38 that is arranged in the housing 36. The non-inflatable seal 70 is shaped for insertion into the stoma 18 in the same way as the stoma seal 22 described previously, except that no inflation or deflation of the stoma seal 70 is involved. The stoma seal 70 is deactivated by withdrawal from the stoma 18 when the second manipulation tab 37 is pulled to move the front wall 14 of the pouch 10 in a direction away from the rear wall 12 and the stoma 18. The foam 39 which is used as the non-inflatable stoma seal 22 can incorporate with particles of activated carbon such that the activated carbon containing foam has the ability to deodorize. Another example of a non-inflatable stoma seal is a tampon-like plug. An introducer to push the tampon inside of stoma 18 can be employed. In both cases of activated carbon containing plug and tampon-like plug, the membrane layer 74 (FIG. 7) could be micro perforated to allow the flatus to pass through without releasing body waste. Furthermore, open cell foam and closed cell foam can be used without the presence of the film 25 in FIG. 4 or film 74 in FIG. 7, including hydrophilic foam. In this example, the hardness of the foam is preferably less than 60 Shore A.

The walls of film membrane 27 in FIG. 4, the walls of film membrane 74 in FIG. 7, and the plug 72 shown in FIG. 7, can be coated with adhesives to enhance the sealing, including hydrocolloid adhesives, mucoadhesives, and other adhesives that are shown to be safe and effective in sealing directly to mucosa membranes.

Figure 8:
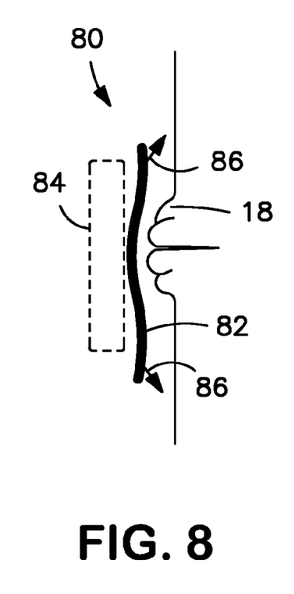
FIG. 8 is a schematic sectional view of a second possible modification of the stoma seal used in the preferred embodiments.

Furthermore, in the above-described embodiments, the stoma seal 22/70 is configured to enter the stoma 18, in order to form a seal against the internal tissue of the stoma 18. Such a seal can be advantageous for a low profile appliance, because the seal need not occupy substantial space outside the stoma 18. However, the invention also contemplates a stoma seal 22/70 that is substantially non-entrant into the stoma 18. For example, FIG. 8 illustrates a stoma seal 22/70 in the form of a non-entrant stoma occluder 80 for sealing against the exterior tissue of a stoma. The stoma occluder generally comprises a diaphragm or membrane 82 that is urged against the stoma 18. The membrane 82 may be urged by any suitable means, for example, by an inflatable balloon 84, or by a resilient foam member (also depicted by numeral 84), or by a tensioner for applying tension indicated by arrows 86.

Although in the preferred embodiments, an appliance is described using a body waste collector in the form a pouch, other shapes and configurations of collector may be used as desired.

It will be appreciated that modifications, improvements and equivalents may fall within the scope of the invention as claimed.

We claim:
1. A controlled evacuation ostomy appliance comprising:
 a. a pouch including a first wall and a second wall, the first wall including a first aperture for receiving a stoma, the first wall made of flexible sheet or material;
 b. a stoma seal located at the first aperture and attached to the second wall, the second wall made of flexible sheet or film;
 c. an inner coupling element positioned at the first aperture and attached to the stoma seal; and
 d. an outer coupling element attached to the first wall, the inner coupling element disposed inwardly and substantially surrounded by the outer coupling element, and wherein the outer and inner coupling elements are frangibly connected.
2. The controlled evacuation ostomy appliance of claim 1, further comprising a stoma seal support attached to the stoma seal.
3. The controlled evacuation ostomy appliance of claim 1, further comprising a stoma seal support attached to the second wall.
4. The controlled evacuation ostomy appliance of claim 1, wherein the outer and inner coupling elements are integral with each other.
5. The controlled evacuation ostomy appliance of claim 1, wherein the inner coupling element is arranged within the outer coupling element.
6. The controlled evacuation ostomy appliance of claim 1, further comprising a first manipulation tab associated with the outer coupling element, and a second manipulation tab associated with the inner coupling element.
7. The controlled evacuation ostomy appliance of claim 6, wherein the first and second manipulation tabs permit application of a force on one coupling element relative to the other.
8. The controlled evacuation ostomy appliance of claim 2, wherein the stoma seal support further comprises a housing attached to the second wall, the housing being of a material more rigid than the second wall.
9. The controlled evacuation ostomy appliance of claim 8, wherein the housing includes a foam member.
10. The controlled evacuation ostomy appliance of claim 8, wherein the housing includes a deodorizing filter.
11. The controlled evacuation ostomy appliance of claim 8, wherein the housing is at least partly domed.
12. The controlled evacuation ostomy appliance of claim 1, wherein the stoma seal is of a type insertable into the stoma for sealing against an internal surface.
13. The controlled evacuation ostomy appliance of claim 12, wherein the insertable stoma seal includes a foam member.
14. The controlled evacuation ostomy appliance of claim 12, wherein the insertable stoma seal includes a foam member and activated carbon.
15. The controlled evacuation ostomy appliance of claim 12, wherein the insertable stoma seal includes a hydrophilic foam.
16. The controlled evacuation ostomy appliance of claim 12, wherein the insertable stoma seal is of a tampon type.
17. The controlled evacuation ostomy appliance of claim 1, wherein the stoma seal is of a type comprising an occluder for sealing against an external surface of a stoma.
18. The controlled evacuation ostomy appliance of claim 1, wherein the stoma seal is inflatable.
19. The controlled evacuation ostomy appliance of claim 18, wherein the stoma seal comprises silicone, polyurethane, synthetic rubber or blends thereof.

20. The controlled evacuation ostomy appliance of claim 1, wherein a surface of the stoma seal capable of contact with peristomal skin is coated with an adhesive.

21. The controlled evacuation ostomy appliance of claim 20, wherein the adhesive is comprised of hydrocolloid, mucoadhesives, or blends thereof.

22. The controlled evacuation ostomy appliance of claim 2, wherein the stoma seal and the stoma seal support are permanently attached directly or indirectly to the pouch.

23. The controlled evacuation ostomy appliance of claim 1, wherein the appliance is a one-piece appliance.

24. The controlled evacuation ostomy appliance of claim 1, wherein the appliance is a two-piece appliance, the appliance further comprising a body fitment for adhesive attachment to peristomal skin.

25. A controlled evacuation ostomy appliance comprising:
  a. a collector for collecting body waste, the collector having a first aperture;
  b. an outer coupling element coupled to the collector around the first aperture, for supporting the collector;
  c. a stoma seal for forming a seal against the stoma, the stoma seal being coupled to a portion of the collector generally opposite the first aperture; and
  d. an inner coupling element coupled to the stoma seal for supporting the stoma seal;
    wherein the inner coupling element is frangibly connected to by the outer coupling element.

26. The controlled evacuation ostomy appliance of claim 25, wherein the collector is a pouch.

27. The controlled evacuation ostomy appliance of claim 25, wherein the collector, the outer coupling element, the stoma seal and the inner coupling element are permanently attached one to another.

28. The controlled evacuation ostomy appliance of claim 25, further comprising a first manipulation tab associated with the outer coupling element, and a second manipulation tab associated with the inner coupling element.

29. The controlled evacuation ostomy appliance of claim 25, further comprising a pouch that can be folded up to itself by means of adhesives, or mechanical locking such as hook-loop or hook-hook fasteners, or zipper.

30. The controlled evacuation ostomy appliance of claim 28, wherein the first and second manipulation tabs permit a separation force to be applied to one coupling element relative to the other.

31. An ostomy appliance comprising:
  a. a pouch comprising a first wall and a second wall, the first wall including a first aperture for receiving body waste from a stoma,
  b. an outer coupling element coupled to the first wall and surrounding the first aperture; and
  c. an inner coupling element coupled to the second wall, the inner coupling element being disposed inside and frangibly connected to the outer coupling element.

32. The ostomy appliance of claim 31, wherein the inner and outer coupling elements are substantially coplanar, at least initially.

33. The ostomy appliance of claim 31, wherein the inner and outer coupling elements are integral with each other.

34. The ostomy appliance of claim 31, wherein the inner coupling element is configured for holding the second wall of the pouch close to the first wall, in the region of the first aperture.

35. The ostomy appliance of claim 31, further comprising a first manipulation tab associated with the outer coupling element and a second manipulation tab associated with the inner coupling element.

36. The ostomy appliance of claim 31, wherein the second manipulation tab is attached to the second wall, at a position at or adjacent to, a connection of the inner coupling element to the second wall.

37. The ostomy appliance of claim 36, wherein the first and second manipulation tabs permit a separation force to be applied to one coupling element relative to the other.

38. An ostomy appliance comprising:
  a. a pouch comprising a first wall and a second wall;
  b. a first manipulation tab associated with the first wall;
  c. a second manipulation tab associated with the second wall, and
  d. two frangibly connected coupling elements permitting distension of the pouch upon manipulation of the first manipulation and second manipulation tabs.

39. A controlled evacuation ostomy appliance comprising:
  a. a pouch including a first wall and a second wall, the first wall including a first aperture for receiving a stoma, the first wall made of flexible sheet or film material;
  b. a stoma seal located at the first aperture and attached to the second wall, the second wall made of flexible sheet or film;
  c. a stoma seal support for supporting the stoma seal at the first aperture, comprising an inner coupling element positioned at the first aperture, the inner coupling element attached to the stoma seal;
  d. an outer coupling element attached to the first wall; and
  e. a frangible connection configured to connect the inner coupling element and the outer coupling element,
    wherein the inner coupling element is disposed inwardly and substantially surrounded by the outer coupling element, and
    wherein the frangible connection breaks or starts to break when the inner coupling element moves away from the outer coupling element.

* * * * *